United States Patent
Sogabe et al.

(10) Patent No.: US 7,618,800 B2
(45) Date of Patent: Nov. 17, 2009

(54) GLYCEROL KINASE, WHICH HAS HIGH RESISTANCE AGAINST PRESERVATIVE

(75) Inventors: Atsushi Sogabe, Fukui (JP); Masanori Oka, Fukui (JP); Kenji Inagaki, Okayama (JP); Takashi Hatta, Okayama (JP); Hiroshi Nishise, Osaka (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 73 days.

(21) Appl. No.: 10/527,370

(22) PCT Filed: Sep. 8, 2003

(86) PCT No.: PCT/JP03/11411

§ 371 (c)(1),
(2), (4) Date: Nov. 28, 2005

(87) PCT Pub. No.: WO2004/024923

PCT Pub. Date: Mar. 25, 2004

(65) Prior Publication Data

US 2006/0166313 A1 Jul. 27, 2006

(30) Foreign Application Priority Data

Sep. 10, 2002 (JP) ............................... 2002-264466

(51) Int. Cl.
*C12N 9/12* (2006.01)
(52) U.S. Cl. ...................................................... 435/194
(58) Field of Classification Search ........................ None
See application file for complete search history.

(56) References Cited

FOREIGN PATENT DOCUMENTS

| JP | 56-121484 | | 9/1981 |
|---|---|---|---|
| WO | WO 95/01292 | * | 1/1995 |

OTHER PUBLICATIONS

Bloch et al. (1980) Journal of Bacteriology, vol. 141, p. 1409-1420.*
Wilkison et al. (1991) The Journal of Biological Chemistry, vol. 266, pp. 16886-16891.*
Bradshaw et al., N-Terminal processing: the methionine aminopeptidase and N-acetyl transferase families., TIBS, 1998, vol. 23, pp. 263-267.*
Cole et al., (1998) "Deciphering the biology of *Microbacterium tuberculosis* from the complete genome sequence.", Nature 393:537-544.
Cole et al., (1998) "Deciphering the biology of *Microbacterium tuberculosis* from the complete genome sequence.", Nature 393:537-544 (Version with corrections ).
Huang et al., "Cloning, Sequencing, High Expression , and Crystallization of the Thermophile *Termus aquaticus* Glycerol Kinase," Biosci. Biotechnol. Biochem. 62(12):2375-2381, 1998.

* cited by examiner

*Primary Examiner*—David J Steadman
*Assistant Examiner*—Alexander D Kim
(74) *Attorney, Agent, or Firm*—Fish & Richardson P.C.

(57) ABSTRACT

The disclosure relates to (i) a gene isolated from *Cellulomonas* sp.JCM2471, the gene encoding a new glycerol kinase and (ii) a method for preparing the glycerol kinase by gene recombination technique, A Glycerol kinase which has high resistance against preservative, a recombinant vector comprising a gene encoding the glycerol kinase, a transformant prepared by transforming a host cell with the recombinant vector, and a method for producing the glycerol kinase, including culturing the transformant to produce glycerol kinase, and collecting the resulting glycerol kinase.

4 Claims, 9 Drawing Sheets

FIG. 8

| STEPS | TOTAL ACTIVITY (KU) | SPECIFIC ACTIVITY (U/mg PROTEIN) | YIELD (%) |
|---|---|---|---|
| SOLUTION AFTER DINOMILL DISRUPTION | 18,000 | 0.31 | 100.0 |
| REDISSOLVED SOLUTION OF AMMONIUM SULFATE PRECIPITATION | 15,516 | 3.0 | 86.2 |
| SEPHADEX G-25 (1) | 15,264 | 5.2 | 84.8 |
| 1ST DEAE SEPHAROSE CL-6B | 12,960 | 32.6 | 72.0 |
| PHENYL SEPHAROSE CL-6B | 10,368 | 32.4 | 57.6 |
| SEPHADEX G-25 (2) | 10,242 | 32.2 | 56.9 |
| 2ND DEAE SEPHAROSE CL-6B | 8,190 | 40.9 | 45.5 |

FIG. 9

| STEPS | TOTAL ACTIVITY (KU) | SPECIFIC ACTIVITY (U/mg PROTEIN) | YIELD (%) |
|---|---|---|---|
| SOLUTION AFTER FRENCH PRESSED DISRUPTION | 6,800 | | 100.0 |
| POLYETHYLENE IMINE SOLUTION | 7,300 | 2.76 | 107.3 |
| REDISSOLVED SOLUTION OF AMMONIUM SULFATE PRECIPITATION | 7,100 | 8.51 | 104.4 |
| SEPHADEX G-25 (1) | 5,100 | 7.85 | 75.0 |
| HITRAP Q | 4,850 | 25.7 | 71.3 |
| HITRAP PHENYL FF | 5,300 | 41.2 | 77.9 |
| SEPHADEX G-25 (2) | 5,200 | 41.2 | 76.4 |

…

GLYCEROL KINASE, WHICH HAS HIGH RESISTANCE AGAINST PRESERVATIVE

TECHNICAL FIELD

The present invention relates to a gene encoding a novel glycerol kinase and a method for preparing the enzyme by a gene recombination technique.

BACKGROUND OF THE INVENTION

A glycerol kinase (EC 2. 7. 1. 30) is an enzyme catalyzing the reaction for modifying glycerol into glycerol-3-phosphoric acid via phosphorylation reaction depending on magnesium and ATP. Since a glycerol kinase had discovered in liver by Kalckar in 1937 (see for example non-patent reference 1), it has been reported the purification of glycerol kinase from such as rat liver, pigeon liver, Candida mycoderma, Cellulomonas flavigena, Thermus flavus (see for example non-patent references 2 to 5 and patent reference 1). It has been known that the glycerol kinase exists widely in general biological organisms. Additionally, it has also been reported that gene cloning from such as human, Bacillus subtilis, Saccharomyces cerevisiae and Thermus flavus (see for example non-patent references 6 to 9). The enzyme has been studied in detail in Escherichia coli in particular. In 1967, Hayashi et al. purified the enzyme (see for example non-patent reference 10). In 1988, the cloning thereof was reported (see for example non-patent reference 11). Further, the enzyme has been studied in a wide range including research works on gene regulation and research works about the inhibition with allosteric inhibitors.

On the other hand, with regard to the industrial application of the glycerol kinase, the glycerol kinase is now used as a raw material enzyme for clinical laboratory agents. In other words, neutral fat (triglyceride) in a sample is hydrolyzed with lipase to prepare glycerol, which is then modified into glycerol-3-phosphoric acid with the enzyme. The resulting glycerol-3-phosphoric acid is used for assaying blood neutral lipid by calorimetric analysis using an oxidase of glycerol-3-phosphoric acid and ultraviolet absorptiometry using dehydrogenase of glycerol-3-phosphoric acid.

Recent clinical laboratory agents for biochemical tests have mainly been laboratory agents at solution state. Therefore, it is demanded that such laboratory agents in liquid should have high stability in addition to the characteristic features (high reactivity with substrates, strict substrate specificity, etc.) traditionally demanded for enzymes. Various characteristic features contributing to the stability of test agents in liquid can be suggested. Generally, preservative is added so as to enable long-term storage of test agents in liquid. Since such preservative may sometimes make enzymes unstable, high resistance against preservative is one of desirable enzyme properties for test agents.

It has been believed so far that enzymes which have high thermal stability show high stability in test agents in liquid. Therefore, a glycerol kinase derived from thermophilic bacteria such as Bacillus stearothermophilus and Thermus flavus has been commonly used. However, such glycerol kinase has a problem of low resistance against preservative.

Patent reference 1: JP-A-56-121484
Non-patent reference 1: H. Kalckar, eds., "Enzymologia", Vol.2, p. 47, 1937
Non-patent reference 2: C. Bublitz, et al., "J. Biol. Chem.", Vol. 211, p. 951, 1954
Non-patent reference 3: E. P. Kennedy, "Methods Enzymol.", Vol. 5, p. 476, 1962
Non-patent reference 4: H. U. Bergmeyer, et al., "Biochem.", Vol. 333, p. 471, 1961
Non-patent reference 5: H. S. Huang, et al., "J. Ferment. Bioeng.", No. 83, p. 328, 1997
Non-patent reference 6: C. A. Sargent, et al., "Hum. Mol. Genet.", Vol. 3, p. 1317, 1994
Non-patent reference 7: C. Holmberg, et al., "J. Gen. Microbiol.", Vol. 136, p. 2367, 1990
Non-patent reference 8: P. Pavlik, et al., "Curr. Genet.", Vol. 24, p. 21, 1993
Non-patent reference 9: H. S. Huang, et al., "Biochim. Biophys. Acta", Vol. 1382, p. 186, 1998
Non-patent reference 10: S. Hayashi, et al., "J. Biol. Chem.", Vol. 242, p. 1030, 1967
Non-patent reference 11: D. W. Pettigrew, et al., "J. Biol. Chem.", Vol. 263, p. 135, 1988

BRIEF DESCRIPTION OF THE DRAWINGS

FIG. 8 shows the result of the purification of glycerol kinase from *Cellulomonas* sp. JCM2471 in Reference Example.

FIG. 9 shows the result of purification of glycerol kinase obtained in Example of the present invention.

DISCLOSURE OF THE INVENTION

Figure 1:
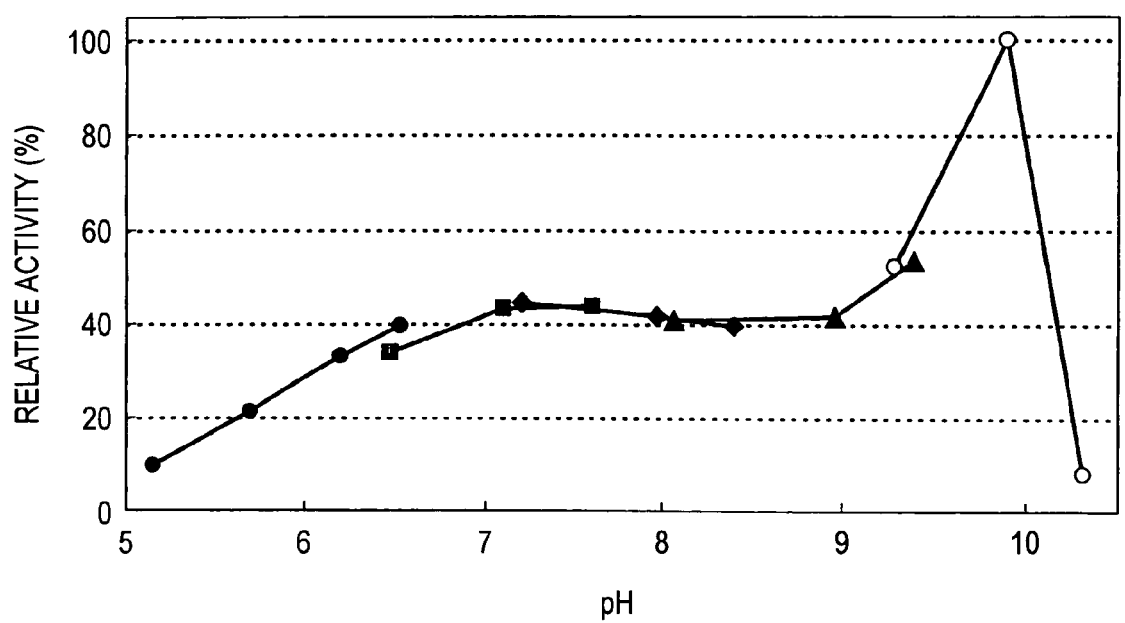
FIG. 1 shows the relation between the reaction pH of glycerol kinase obtained in an Example of the present invention and the relative activity thereof (namely, optimum pH). Glycerol kinase activity was assayed after reaction in each 50 mM buffer at 37° C. for 5 minutes. The horizontal axis shows pH, while the vertical axis shows relative activity. Black circles express the reaction in the presence of 50 mM MES buffer; black squares express the reaction in the presence of 50 mM HEPES buffer; black diamonds express the reaction in the presence of TAPS buffer; black triangles express the reaction in the presence of 50 mM CHES buffer; and white circles express the reaction in the presence of 50 mM glycine-NaOH.

By isolating a gene encoding a novel glycerol kinase which has high resistance against preservative and establishing a method for producing the enzyme by gene recombination technique, the enzyme can be applied to the quantitative assay of neutral lipid and glycerol.

In order to solve the problems, the inventors of the present invention made investigations. Consequently, the novel glycerol kinase which has high resistance against preservative could successfully be isolated. Specifically, *Cellulomonas* sp. JCM2471 was isolated as a bacterium which produces such glycerol kinase. The glycerol kinase gene was successfully isolated from the chromosomal DNA extracted from the bacterium, to determine the whole nucleotide sequence of the DNA. Furthermore, glycerol kinase was highly produced in a transformant by gene recombination technique to enable large-scale supply of glycerol kinase of high purity at low cost. The bacterial strain can be purchased from Riken Bioresource Center in Bioscience Technology Center, Riken.

In other words, the present invention provides glycerol kinase and the like as described below.

Item 1 A glycerol kinase which has high resistance against preservative.

Item 2 The glycerol kinase according to item 1, wherein the resistance against preservative expressed as a remaining activity ratio is 70% or more when the glycerol kinase coexists with the 100 mg/L concentration of preservative at 25° C. for one week.

Item 3 The glycerol kinase according to item 1 or 2, in which the preservative is N-methylisothiazolone and/or a derivative thereof.

Item 4 The glycerol kinase according to item 1, which is a protein of (a) or (b) below:
(a) a protein consisting of an amino acid sequence represented by SEQ ID NO:1 in the Sequence Listing; or
(b) a protein comprising an amino acid sequence of the amino acid sequence (a) in which one or several amino acids are deleted, substituted or added and having glycerol kinase activity.

Item 5 A gene encoding a glycerol kinase which is a protein consisting of an amino acid represented by SEQ ID NO:1 in the Sequence Listing.

Item 6 A gene encoding glycerol kinase consisting of DNA of (c) or (d) below:
(c) a DNA consisting of a nucleotide sequence represented by SEQ ID NO:2 in the Sequence Listing; or
(d) a DNA comprising a nucleotide sequence of the nucleotide sequence (c) wherein one or several nucleotides are added, deleted or substituted and encoding a protein having glycerol kinase activity.

Item 7 A recombinant vector comprising a gene encoding the glycerol kinase according to any one of items 1, 2 or 3.

Item 8 A transformant comprising a host cell transformed with the recombinant vector according to item 7.

Item 9 A method for preparing a glycerol kinase, which comprises culturing the transformant according to item 8 to produce a glycerol kinase, and collecting the glycerol kinase.

The glycerol kinase of the present invention comprises a glycerol kinase which has high resistance against preservative.

Additionally, the present invention relates to glycerol kinase wherein the resistance against preservative, expressed as a remaining activity ratio is 70% or more, preferably 80% or more, more preferably 90% or more, when the glycerol kinase coexists preservative in concentration of 100 mg/L at 25° C. for one week.

The resistance against preservative in the present invention can be evaluated on the basis of the remaining activity ratio when about 5 U/mL glycerol kinase coexists with preservative at 25° C. for one week in 50 mM potassium phosphate buffer of pH 7.5.

The term preservative means a substance which is added to a reagent during storage for the purpose of suppressing the growth of microorganisms therein. The concentration of the preservative added is not specifically limited, and preferably concentration which gives sufficient effect. Reasonably, the concentration of a preservative to be added varies depending on the type of the preservative and the composition of a reagent to be added. A person skilled in the art can appropriately determine suitable concentration of the preservative to be added.

Taking account of concerns against the generation of resistant bacteria during the use of antibiotics, the use of antibiotics is considered undesirable except for a case really demanding the use thereof. Additionally, no preservative effect may sometimes be obtained because of the influence of existing resistant bacteria. On the other hand, a preservative which can act on protein directly is more preferable, since it is difficult for microorganisms to acquire resistance against such preservative. Therefore, there is high possibility that such preservative may be used commonly in future. Such preservatives include such as N-methylisothiazolone (abbreviated as MIT) and/or a derivative thereof. Since such preservative which has direct actions on protein also work spontaneously coexisting enzyme protein, there is possibility that the preservative may make the enzyme protein unstable, depending on the structure thereof. As described above, the resistance against preservative may be derived from both the function mechanism of the preservative and the protein structure.

The gene encoding the glycerol kinase of the present invention may be extracted from microorganisms which produce glycerol kinase, for example *Cellulomonas* sp. JCM2471 or may chemically be synthesized.

The gene includes such as (a) a DNA encoding the protein consisting of the amino acid sequence represented by SEQ ID NO:1, or (b) a DNA encoding the protein comprising an amino acid sequence in which one or several amino acids in the amino acid sequence (a) is deleted, substituted or added and having glycerol kinase activity. As to the degree of the deletion, substitution or addition in the DNA, the resulting DNAs should have the fundamental characteristic properties of the intact DNA without any modification or should have improvement in the characteristic properties of the intact DNA. The method for preparing such variants is according to traditionally known methods.

Otherwise, the gene includes for example (c) a DNA consisting of the nucleotide sequence of SEQ ID NO:2, or (d) a DNA comprising a nucleotide sequence in which one or several nucleotides in the nucleotide sequence (c) is deleted, substituted or added and encoding a protein which has glycerol kinase activity.

The method for obtaining the gene encoding the glycerol kinase of the present invention is described below as example. After separating and purifying the chromosomal DNA of *Cellulomonas* sp. JCM2471, the DNA is fragmented using ultrasonic disruption or restriction treatment or the like and ligated with a linear expression vector at the cohesive ends or adhesive ends of the both DNA fragments, by closing ring to construct a recombinant vector. The resulting recombinant vector thus obtained is transfected into a replicable host microorganism. Subsequently, the resulting transformants are screened using the expression of glycerol kinase activity to obtain a microorganism carrying the recombinant vector. Then, the microorganism is cultured to separate and purify the recombinant vector from the cultured microorganism and isolate the glycerol kinase gene from the recombinant vector.

The DNA from *Cellulomonas* sp. JCM2471 as a donor of the gene is specifically collected as described below. Namely, the donor microorganism is for example cultured under shaking for one day to three day(s) and collected by the centrifugation. The resulting microorganism is subjected to lysis, to prepare a lytic material containing the glycerol kinase gene. As the lytic method, the microorganism is treated with for example lytic enzymes such as lysozyme and β-glucanase, in combination with protease, other enzymes and detergents such as sodium lauryl sulfate (SDS), if necessary, and also in combination with physical disruption processes such as freeze thawing and French press process.

A separation and purification of the DNA from the lytic material thus obtained can be carried out by for example, appropriate combinations of conventional processes including deproteinization such as phenol treatment and protease treatment, ribonuclease treatment, and alcohol precipitation treatment.

Further, the DNA can efficiently be obtained at high purify, using various DNA extraction kits which is currently commercially available.

As the method for cleaving the DNA separated and purified from the microorganism, for example, ultrasonification and restriction enzyme treatment can be carried out. Type II restriction enzymes which act on specific nucleotide sequences are preferable.

As the vector, vectors constructed from phage or plasmid autonomously replicable in host microorganisms for gene recombination are suitable. As the phage, for example, lambda ZAPII (manufactured by Stratagene), λgt•10, and λgt•11 can be used when *Escherichia coli* is a host microorganism. As the plasmid, for example, pBR322, pUC19, pBluescript, pUCBM20, pUCBM21, pSE280 and pSE380 can be used when *Escherichia coli* (*E. coli*) is a host microorganism.

Such vector can be obtained by cleavage with restriction enzymes used for the cleavage of the microbial DNA as a donor of the glycerol kinase gene to prepare a vector fragment. However, the same restriction enzyme of the restriction enzyme used for cleaving the microbial DNA is not necessarily used. As the method for conjugating the microbial DNA fragment to the vector DNA fragment, a known method using DNA ligase can be carried out. For example, after annealing with the adhesive end of the microbial DNA fragment, a recombinant vector of the microbial DNA fragment and the vector DNA fragment is prepared by the use of an appropriate DNA ligase. After annealing, if necessary, the vector DNA fragment is transfected in a host microorganism to prepare a recombinant vector using a biological DNA ligase.

As the host microorganism, any microorganism can be used, as long as the resulting recombinant vector is stable and autonomously replicable to express an exogenous gene. Generally, for example, *Escherichia coli* (*E. coli*) strain K-12, *Escherichia coli* (*E. coli*) strain W3110, *Escherichia coli* (*E. coli*) strain C600, *Escherichia coli* (*E. coli*) strain HB101, and *Escherichia coli* (*E. coli*) strain JM109 can be used. Additionally, a variant in which glycerol kinase is deficient is more preferably used as a host, although the activity of glycerol kinase derived from the host is as low as negligible in a glycerol-free culture medium. *Escherichia coli* (*E. coli*) strain KM1 may also be used.

As the method for transfecting the recombinant vector in a host microorganism, competent cell method with calcium treatment and electroporation can be used when *Escherichia coli* (*E. coli*) is a host microorganism. Additionally, commercially available various *Escherichia coli*-competent cells can also be used. By culturing the microorganism thus obtained as a transformant in a nutritious culture medium a great amount of glycerol kinase is produced stably. As to the selection based on the presence or absence of the transfection of the intended recombinant vector into a host microorganism, a microorganism simultaneously expressing drug resistant markers of the vector carrying the intended DNA and glycerol kinase activity can be screened for. For example, a microorganism growing on a selective culture medium based on the drug resistant markers and producing glycerol kinase may be selected.

The nucleotide sequence of the glycerol kinase gene thus obtained by the method can be analyzed by commercially available reagents and automatic sequencers based on the dideoxy method described in Science (*Science*, 214, 1205-1210, 1981) and improved methods thereof. Additionally, the amino acid sequence of glycerol kinase was assumed on the basis of the determined nucleotide sequence. The recombinant vector carrying the glycerol kinase gene as once selected can be recovered from the transformant microorganism, which can easily be transfected into another microorganism. Additionally, DNA as the glycerol kinase gene can be recovered from the recombinant vector carrying the glycerol kinase gene by restriction enzyme and PCR method, which is then conjugated to another vector fragment and transfected into a host microorganism easily.

As the mode for culturing a host microorganism as the transformant, the culture conditions therefore can be selected, taking account of the nutritional and physiological properties of the host. Generally, in most cases, the host microorganism is cultured in liquid. Industrially, such host microorganism is advantageously aeration cultured with aeration and shaking. As a carbon source in the culture medium, carbon sources usually used for microbial culture are widely used. Any carbon sources assimilable by host microorganisms can be used and include such as glucose, sucrose, lactose, maltose, fructose, molasses, and pyruvic acid. As a nitrogen source, nitrogen compounds which can be used by the host microorganism can be used and include such as organic nitrogen compounds such as peptone, meat extract, casein hydrolysate, and soybean bran alkali extracts; and inorganic nitrogen compounds such as ammonium sulfate and ammonium chloride. Besides, salts such as phosphate salts, carbonate salts, sulfate salts, salts of magnesium, calcium, potassium, iron, manganese and zinc, specific amino acids, and specific vitamins can be used if necessary.

The culture temperature can appropriately be changed within a range wherein the host microorganism grows and glycerol kinase is produced. In case of Escherichia coli (E. coli), preferably, the culture temperature is preferably about 20 to 42° C. The culturing time changes more or less, depending on the culture conditions. Culturing may be terminated in appropriate timing when the yield of glycerol kinase is estimated to reach maximum. Generally, the time is about 20 to 48 hours. The pH of the culture medium can appropriately be changed within a range wherein the host microorganism to grow and for glycerol kinase is produced. Generally, preferably, the pH is about 6.0 to 9.0.

The method for recovering the bacterial cell from the liquid culture is in accordance with methods generally used. For example, the bacterial cell can be recovered by centrifugation or filtration. In case that glycerol kinase in the liquid culture is extracellularly secreted, a solution separated from the bacterial cell may can be used. According to the following method after the disruption of the bacterial cell, glycerol kinase can be separated and purified. In case that glycerol kinase exists intracellularly, glycerol kinase can be extracted via enzymatic or physical disruption methods as described above. A fraction of glycerol kinase is recovered from the crude enzyme extract solution thus obtained by for example ammonium sulfate precipitation. The crude enzyme solution is generally desalted by routine purification methods, for example dialysis using semi-permeable membrane or gel filtration on Sephadex G-25 (Amersham Biosciences).

After the procedure, a crude enzyme specimen can be obtained by separation and purification with phenyl Sepharose First Flow (Amersham Biosciences) column chromatography and DEAE-Sepharose First Flow (Amersham Biosciences) column chromatography. The resulting purified enzyme specimen is purified at such a degree that the specimen shows an almost single band by electrophoresis (SDS-PAGE).

The protein which has glycerol kinase activity obtained by the method of the present invention has the following physico-chemical properties described below.

(1) Function: Glycerol+ATP↔Glycerol-3-phophoric acid+ADP (2) Optimal pH: about 10.0

(3) Optimal temperature: about 50° C. (reaction in 20 mM HEPES buffer, pH 7.9 for 5 minutes)

(4) pH stability: about 6.0-10.0 (the range involving the remaining activity of 90% or more even after 20 hr treatment at 25° C.)

(5) Thermal stability: about 45° C. or less (the range involving the remaining activity of 90% or more in 50 mM potassium phosphate buffer, pH 7.5 even after 15-min treatment)

(6) Molecular weight: about 55,000 (SDS-PAGE), about 176,000 (gel filtration)

(7) Km value: about $6.9 \times 10^{-6}$ M (glycerol), about $1.11 \times 10^{-4}$ M (ATP)

(8) Relative activity: about 41.2/mg (9) The remaining activity ratios under storage at 4° C. for one week and at 25° C. for one week when the protein coexists with 100 mg/L MIT in 50 mM potassium phosphate buffer of pH 7.5 was almost 100% (FIG. 5) and about 92% (FIG. 6), respectively.

The glycerol kinase of the present invention may exist in any form, with no specific limitation. If necessary, the glycerol kinase of the present invention may be in a freeze-dried form, a liquid form or any other forms. In case of freeze-drying, additionally, suitable excipients, stabilizers and the like may be added. In case of the liquid form, furthermore, suitable buffers and/or other ingredients may be added.

BEST MODE FOR CARRYING OUT THE INVENTION

In the following Examples, the activity of glycerol kinase was assayed as follows. ATP was purchased from Oriental Yeast Co., Ltd. Bovine serum albumin was purchased from Sigma Aldrich. Oxidase of glycerol-3-phosphoric acid (Code No. G30-301) and peroxidase (Code No. PE0-301) manufactured by Toyobo Co., Ltd. were used. Other reagents were purchased from Nakarai Tesque for use.

<Assay Method 1: Method for Assaying Glycerol Kinase Activity by Rate Assay>

Generally, the activity was assayed by the method. Using glycerol as substrate, the enzyme activity was assayed on the basis of the amount of produced glycerol-3-phosphoric acid. By adding 0.1 M HEPES buffer of pH 7.9 to 0.2 ml of 0.5% 4-aminoantipyrine solution, 0.2 ml of 1.5% phenol solution, 200 U of the oxidase of glycerol-3-phosphoric acid, 80 U of peroxidase, and 48.4 mg of ATP, a total volume is adjusted to be 21 ml. The resulting solution was used as the stock solution for the following assays. To 3 ml of the assay stock solution, 50 µl of 0.3 M glycerol solution and 100 µl of the enzyme solution were added and mixed. Each reaction was assayed by recording the absorbance at 500 nm for 3 minutes with a spectrophotometer which is controlled to be 37° C., and calculating the change of the absorbance per minute on the initial linear part (triangle OD test). A blank test was conducted by adding 100 µl of a diluted enzyme solution (20 mM potassium phosphate buffer of pH 7.5 containing 0.2% bovine serum albumin) instead of the enzyme solution and carrying out the same procedures as described above and calculating the change of the absorbance per minute (triangle OD blank).

Based on the change of the absorbance as obtained, the enzyme activity of glycerol kinase was calculated according to the following formula. Additionally, one unit (1 U) of the enzyme was defined as an amount thereof required for the phosphorylation of 1 µmol glycerol per minute under the aforementioned conditions.

Formula

Activity value (U/ml)=[triangle OD/min (triangle ODtest-triangle ODblank)×3.15 (ml)×dilution ratio]/[13.3×½×1.0 (cm)×0.1 (ml)]

3.15 ml=volume of reaction mixture solution 13.3=extinction coefficient per millimole quinone dye under the aforementioned assay conditions ½=coefficient due to the quinone dye amount formed from one molecule of aqueous hydrogen peroxide produced via the enzyme reaction, which is ½ molecule.

1.0 cm=optical path of cell 0.1 ml=volume of enzyme sample

<Assay Method 2: Method for Assaying Optimal Temperature>

The method was used so as to find the optimal temperature for the enzyme.

After dividing 3 ml of an active reaction solution (20 mM HEPES buffer of pH 7.9 containing 4 mM ATP and 2 mM magnesium chloride) in a test tube, 0.1 ml of a glycerol kinase solution after dilution to an appropriate concentration (about 1 U/ml of the activity measured according to the assay method 1) was added thereto and mixed thoroughly. Then, the reaction mixture is preliminarily heated at each temperature for about 3 minutes. Then, 0.05 ml of aqueous 0.3 M glycerol solution was added and mixed for initiating the reaction. After the reaction for exact 10 minutes, 1 ml of 1N hydrochloric acid was added to terminate the enzyme reaction. After adding 0.15 ml of the reaction-terminated solution to 3 ml of a chromogenic solution (0.2 M HEPES buffer of pH 7.9 containing 0.01% 4-aminoantipyrin, 0.02% phenol, 5 U/ml peroxidase and 16 U/ml glycerol-3-phosphoric acid oxidase) and mixing, reaction at 37° C. for about 5 minutes was carried out to measure the absorbance at 500 nm. Then, the absorbance of 1 mM L-glycerol-3-phosphoric acid solution was simultaneously measured. The amount of L-glycerol-3-phosphoric acid produced via each of the reactions was determined. Herein, a blank test was carried out by determining the amount of L-glycerol-3-phosphoric acid produced in an unspecific manner at each reaction temperature, using the diluted enzyme solution instead of the glycerol kinase solution.

<Assay Method 3: Method for Assaying Optimal pH>

The method was used so as to examine the optimal pH of the enzyme.

After dividing 3 ml of an active reaction solution (50 mM buffer at each pH, containing 4 mM ATP and 2 mM magnesium chloride) in a test tube, 0.1 ml of a glycerol kinase solution after dilution to an appropriate concentration (about 1 U/ml of the activity measured according to the assay method 1) was added thereto and mixed thoroughly. Then, the reaction mixture is preliminarily heated at 37° C. for about 3 minutes. Then, 0.05 ml of 0.3 M glycerol solution was added and mixed for initiating the reaction. After reaction for exact 10 minutes, 1 ml of 1N hydrochloric acid was added to terminate the enzyme reaction. After adding 0.15 ml of the reaction-terminated solution to 3 ml of a chromogenic solution (0.2 M HEPES buffer of pH 7.9 containing 0.01% 4-aminoantipyrin, 0.02% phenol, 5 U/ml peroxidase and 16 U/ml glycerol-3-phosphoric acid oxidase) and mixing, reaction at 37° C. for about 5 minutes was carried out to measure the absorbance at 500 nm. Then, the absorbance of 1 mM L-glycerol-3-phosphoric acid solution was simultaneously measured. The amount of L-glycerol-3-phosphoric acid produced via each enzyme reaction was determined. Herein, a blank test was carried out by determining the amount of L-glycerol-3-phosphoric acid produced in the buffer at each pH in an unspecific manner without any enzymatic reaction, using the diluted enzyme solution instead of the glycerol kinase solution.

REFERENCE EXAMPLE

Purification of Glycerol Kinase from *Cellulomonas* sp. JCM2471

After inoculating one platinum loop of *Cellulomonas* sp. JCM2471 in 60 ml of the LB liquid culture medium (in 500-mL Sakaguchi's flask), culturing with shaking at 30° C. overnight was carried out. The liquid culture was wholly inoculated in a 6 L of culture medium for glycerol kinase production (10 L-jar fermenter, 2% glycerol, 2% polypeptone (manufactured by Nihon Pharmaceutical Co., Ltd.), 0.2% yeast extract (manufactured by Oriental Yeast Co., Ltd.), 0.2% NaCl, 0.02% magnesium sulfate, 0.7% dipotassium phosphate, pH 7.3) and cultured with shaking and aeration at 35° C. for about 20 hours. The amount of glycerol kinase produced per the culture medium was about 3 U/ml.

The bacterial cell was recovered by centrifugation from the liquid culture, suspended in 50 mM potassium phosphate buffer of pH 7.5 and disrupted with glass beads using a Dinomill disrupter to extract glycerol kinase, which was used as crude enzyme solution. Ammonium sulfate was added to the crude enzyme solution, from which a 35-55% saturated fraction was recovered. This fraction after salting out was desalted by gel filtration with Sephadex G-25 (Amersham Biosciences), and subjected sequentially to DEAE Sepharose CL-6B (Amersham Biosciences) column chromatography, phenyl Sepharose CL-6B (Amersham Biosciences) column chromatography, gel filtration with Sephadex G-25 and DEAE Sepharose CL-6B column chromatography, to recover a purified enzyme specimen. The purification results are shown in FIG. 8.

The protein purified by the aforementioned method shows an almost uniform band on SDS-PAGE, and had a relative activity of about 40.9 U/mg protein. Additionally, the protein concentration was approximately calculated by defining that 1 mg/ml protein concentration corresponded to 1 Abs absorbance of the enzyme solution at 280 nm.

Additionally, the molecular weight of the subunit estimated by SDS-PAGE was about 55,000. Further, the N-terminal amino acid sequence was analyzed by an amino acid sequencer based on the principle Edman degradation method. The sequence from the N terminus was Ala-Asp-Tyr-Val-Leu-Ala-Ile (amino acid residues 2-8 of SEQ ID NO:1).

Example 1

Separation of Chromosomal DNA from *Cellulomonas* sp. JCM2471

The chromosomal DNA of *Cellulomonas* sp. JCM2471 was separated by the following method. One platinum loop of the bacterial strain was inoculated in an LB culture broth (5 ml charged amount/30-ml test tube; 1.0% polypeptone, 0.5% yeast extract, 1.0% NaCl, pH 7.4) and cultured with shaking at 30° C. for overnight. The bacterial cell was recovered from 1 ml of the bacterial cell by centrifugation (12,000 rpm, 10 minutes, 4° C.). The chromosomal DNA was extracted from the recovered bacterial cell, using MagExtractor-genome kit (manufactured by Toyobo Co., Ltd.) according to the procedures described in the manual. The chromosomal DNA was obtained at about 20 µg from 1 ml of the bacterial cell.

Example 2

Amplification of Glycerol Kinase Gene by PCR

Primers for polymerase chain reaction (PCR) were prepared on the basis of the nucleotide sequences of glycerol kinase from *Escherichia coli* (*E. coli*), *Bacillus subtilis*, and *Pseudomonas aeruginosa*, of which their cloning is currently reported. The nucleotide sequences of SEQ ID NO:3 in the sequence listing and SEQ ID NO:4 in the sequence listing show the PCR primers. By mixing 100 ng of the DNA obtained in Example 1, 200 pmol of each of the primers, 10 μl of a dNTP mixture, 10 μl of a reaction buffer, and 2.5 U of AmpliTaq DNA polymerase (manufactured by Perkin Elmer), a final volume of reaction liquid mixture was adjusted to be 100 μl. This was subjected to PCR including repeating 30 times of a cycle of a modification reaction at 94° C. for one minute, an annealing reaction at 45° C. for one minute and an extension reaction at 72° C. for 3 minutes. Consequently, a fragment of about 800 bp as an intended size was amplified. The nucleotide sequence of the PCR product was determined. When the speculated amino acid sequence was compared with the amino acid sequence of glycerol kinase from *Pseudomonas aeruginosa*, high homology was shown. Thus, it was indicated that a part of the intended glycerol kinase gene was amplified.

Example 3

Cloning of Full-Length Glycerol Kinase Gene

About 2 μg of the chromosomal DNA obtained in Example 1 was digested with various restriction enzymes, separated by 0.7% agarose gel electrophoresis and transferred onto a nitrocellulose filter. The filter was subjected to Southern hybridization according to the protocol attached to the reagents, using the PCR product obtained in Example 2 as probe and ECL direct nucleic acid labeling and detection system (Amersham Biosciences), to screen for fragments of the glycerol kinase gene. Consequently, the DNA fragment containing the full-length glycerol kinase gene was detected as a fragment of about 6.5 kb after cleavage with KpnI (manufactured by Toyobo Co., Ltd.) and NotI (manufactured by Toyobo Co., Ltd.).

Then, the DNA fragment was recovered from the agarose gel using MagExtractor-PCR & gel clean up-kit (manufactured by Toyobo Co., Ltd.) according to the procedures described in the manual. Alternatively, 0.5 μg of puCBM21 (Boehringer Mannheim) was similarly cleaved with KpnI and NotI, for dephosphorylation treatment with bacterial alkali phosphatase (manufactured by Toyobo Co., Ltd.). Subsequently, both the DNA fragments reacted together at 16° C. for one hour using Ligation High kit (manufactured by Toyobo Co., Ltd.) for ligation to transform the competent cell of *Escherichia coli* JM 109 (manufactured by Toyobo Co., Ltd.). The transformant was obtained by spreading the resulting mixture on an LB agar culture medium containing 100 μg/ml ampicillin and culturing overnight at 37° C. This recombinant vector was designated as pCGK1.

Example 4

Determination of Nucleotide Sequence of Gene of Enzyme Glycerol Kinase

Concerning the nucleotide sequence of the glycerol kinase gene cloned in pCGK1, the DNA sequence was determined starting from both the ends of the inserted gene using common primers for sequencing of pUC-series vectors and big diterminator cycle sequencing FS ready reaction kit (manufactured by Applied BioSystems) and ABI PRISM 310 Genetic Analyzer (manufactured by Perkin Elmer). Further, additional primers were prepared on the basis of the determined sequence to determine the full-length inserted DNA sequence by primer walking.

The DNA sequence corresponding to the open reading frame of the determined glycerol kinase gene and the amino acid sequence speculated on the basis of the DNA sequence are shown as SEQ ID NO:2 in the sequence listing. Additionally, the sequence of seven residues in the amino acid sequence including Ala in the second residue speculated from the DNA sequence was completely corresponds to the result of the amino acid sequencing of the purified enzyme. Furthermore, the molecular weight of glycerol kinase as calculated on the basis of the speculated amino acid sequence from which methionine as the initiation codon was eliminated was 55, 142. The molecular weight corresponds well with the molecular weight of the enzyme purified from *Cellulomonas* sp. JCM2471 which is determined by SDS-PAGE analysis.

Example 5

Construction of Glycerol-Deficient Host

Primers of SEQ ID NO:5 in the sequence listing and SEQ ID NO:6 in the sequence listing were prepared on the basis of the nucleotide sequence of glycerol kinase derived from *Escherichia coli* (*E. coli*) which is registered on the GenBank database. Furthermore, the chromosomal DNA of *Escherichia coli* (*E. coli*) strain K12 was obtained by the same method as in Example 1.

By mixing 100 ng of the chromosomal DNA, 200 pmol of each of the primers, 10 μl of 2mM dNTP mixture, 10 μl of a reaction buffer, and 2.5 U of AmpliTaq DNA polymerase (manufactured by Perkin Elmer), a final volume of the mixture was adjusted to be 100 μl. This was subjected to PCR by carrying out 41 times of a cycle of a modification reaction at 94° C. for 3 minutes, a modification reaction at 98° C. for 30 seconds and an annealing/extension reaction at 68° C. for 3 minutes and then carrying out one cycle of a modification reaction at 98° C. for 30 seconds, an annealing/extension reaction at 68° C. for 3 minutes and an extension reaction at 72° C. for 10 minutes. Consequently, a PCR product of about 1.5 kbp in the same size as that of the intended gene was obtained.

After the PCR product was purified using MagExtractor-PCR & gel clean up-kit according to the procedures described in the manual, the reaction of the PCR product of about 0.2 μg with 0.5 μg of pUC19 cleaved with a restriction enzyme SmaI was carried out at 16° C. for one hour using Ligation High kit to transform the competent cell of *Escherichia coli* (*E. coli*) JM 109. The transformant was obtained by spreading the resulting mixture on an LB agar culture medium containing 100 μg/ml ampicillin and cultured overnight at 37° C. This recombinant vector was designated as pUCGK.

The pUCGK was cleaved with a restriction enzyme BstEII (manufactured by Toyobo Co., Ltd.). The cleavage ends thereof were made to be blunt ended using Blunting High kit (manufactured by Toyobo Co., Ltd.), according to the procedures described in the manual. On the other hand, pUCK4 (manufactured by Amersham Biosciences) was cleaved with HincII. After separating DNA fragments containing the kanamycin resistant gene by agarose gel electrophoresis, the DNA fragments was purified and recovered by using MagExtractor-PCR & gel clean up-kit. Reaction of the both fragments was carried out at 16° C. for one hour, using Ligation High kit to transform the competent cell of *E. coli* JM 109. The transformant was obtained by spreading the resulting mixture on an LB agar culture medium containing 100 μg/ml ampicillin and 50 μg/ml kanamycin for overnight culturing at 37° C. The resulting recombinant vector was designated as pUCGKm.

Furthermore, pUCGKm was cleaved with restriction enzymes EcoRI (manufactured by Toyobo Co., Ltd.) and SalI (manufactured by Toyobo Co., Ltd.) to separate a fragment containing the glycerol kinase gene and the kanamycin resistant gene by agarose gel electrophoresis. The fragment was purified and recovered by using MagExtractor-PCR & gel clean up-kit. On the other hand, a temperature sensitive plasmid pCH02 (a derivative from pSC101 plasmid; S. Matsuyama, et al., *J. Mol. Biol.,* 175, 331 (1984)) was also cleaved with EcoRI (manufactured by Toyobo Co., Ltd.) and SalI (manufactured by Toyobo Co., Ltd.), and then reacted with the fragment containing the glycerol kinase gene and the kanamycin resistant gene at 16° C. for one hour with Ligation High kit to transform *Escherichia coli* (*E. coli*) strain K-12 by electroporation using Gene Pulsar (manufactured by Bio-Rad). Herein, the conditions for the electroporation is in accordance with the conditions for *Escherichia coli* (*E. coli*) which is described in the manual for Gene Pulsar. The transformant was obtained by spreading the resulting mixture on an LB agar culture medium containing 100 μg/ml ampicillin and 50 μg/ml kanamycin for overnight culturing at 30° C.

The resulting transformant was inoculated in an LB culture broth containing 50 μg/ml kanamycin (5 ml charged volume/ 20 ml-test tube) and cultured with shaking at 37° C. for 24 hours. The liquid culture was subcultured in a fresh LB culture broth containing kanamycin, repeatedly four times. The liquid culture was diluted with sterile physiological saline, spreaded on an LB agar culture medium containing 50 μg/ml kanamycin to separate single colonies, from which a colony sensitive to ampicillin and resistant against kanamycin was separated and defined as *Escherichia coli* (*E. coli*) strain KM1 (*E. coli* KM1).

The *Escherichia coli* strain KM1 (*E. coli* KM1) was inoculated in Traffic Broth containing 50 μg/ml kanamycin (5 ml charged volume/20-ml test tube; 1.2% polypeptone, 2.4% yeast extract, 0.5% glycerol, 0.231% monopotassium phosphate, 1.254% dipotassium phosphate), for shaking culture at 37° C. for 24 hours. Bacterial cells were recovered from 1 ml of the liquid culture by centrifugation and suspended in 1 ml of 50 mM potassium phosphate buffer of pH 7.5. The bacterial cells in the resulting suspension were disrupted with an ultrasonic disrupter, and centrifuged. Although the resulting supernatant was used as a crude enzyme to assay the activity of glycerol kinase, no significant enzyme activity was detected.

Example 6

Construction of Glycerol Kinase Expression Vector pCGK12 pCGK1 was cleaved with restriction enzymes NcoI (manufactured by Toyobo Co., Ltd.) and NotI, to separate a DNA fragment of about 2 kb by 1% agarose gel electrophoresis, which contained the glycerol kinase gene. Subsequently, the DNA fragment was recovered from the agarose gel using MagExtractor-PCR & gel clean up-kit according to the procedures described in the manual. On the other hand, 0.5 μg of pSE380 (manufactured by Invitrogen) was cleaved with NcoI and NotI, and treated with bacterial alkali phosphatase (manufactured by Toyobo Co., Ltd.) for dephosphorylation. Subsequently, both the DNA fragments reacted with Ligation High kit at 16° C. for one hour for ligation, to transform the competent cell of *Escherichia coli* (*E. coli*) strain JM109. The transformant was obtained by spreading the resulting mixture on an LB agar culture medium containing 100 μg/ml ampicillin and cultured overnight at 37° C. This recombinant vector was designated as pCGK2.

Then, *Escherichia coli* strain JM109 (*E. coli* JM109) transformed with pCGK12 was inoculated in an LB culture broth (5 ml/30-ml charged into test tube) containing 100 μg/ml ampicillin and cultured with shaking at 37° C. overnight. After completion of the culturing, the liquid culture was centrifuged to recover bacterial cells, from which pCGK12 was purified using MagExtractor-Plasmid-kit (manufactured by Toyobo Co., Ltd.). The purified plasmid of about 20 μg was recovered from 5 ml of the bacterial cells.

Furthermore, pCGK12 was adjusted to a concentration of 0.05 μg/>l and introduced into *Escherichia coli* strain KM1 (*E. coli* KM1) which is a glycerol kinase-deficient strain as a host, by electroporation using Gene Pulsar. The transformant was selected in an LB agar culture medium containing 100 μg/ml ampicillin and 50 μg/ml kanamycin, to screen for a colony which is simultaneously resistant against the two types of antibiotics as a transformant after overnight culturing at 30° C. The efficiency of transformation then was about $1 \times 10^6$ cfu/μg-DNA.

Herein, *Escherichia coli* strain KM1 (pCGK12) (*E. coli* KM1 (pCGK12)) as the transformant was deposited under an accession number of FERM P-18992 at International Patent Organism Depository, National Institute of Advanced Industrial Science and Technology on Sep. 3, 2002.

Example 7

Expression of Recombinant Glycerol Kinase and Recovery of Purified Enzyme

One platinum loop of the transformant obtained in Example 6 was inoculated in an LB culture medium (5 ml charged volume/20-ml test tube) containing 100 μg/ml ampicillin and 50 μg/ml kanamycin and cultured with shaking at 30° C. overnight, to obtain a seed liquid culture. The liquid culture was inoculated at 1% in 1 L-Traffic Broth (250 ml charged volume)/2 L-Sakaguchi's flask per one bottle) containing 100 μg/ml ampicillin and 50 μg/ml kanamycin, and cultured with shaking at 37° C. for 20 hours. At the time of the completion of the culturing, the glycerol kinase activity was about 6.8 U/ml of liquid culture.

After recovering the bacterial cells from the liquid culture by centrifugation, the bacterial cells were suspended in 50 mM potassium phosphate buffer of pH 7.5 and homogenized with French press. Subsequently, NaCl was dissolved in the solution of the homogenized bacterial cells to become 0.1 M to which 5% polyethylene imine solution was added to 0.5% of the solution. Then, insoluble matters were removed from the resulting mixture by centrifugation. The resulting supernatant was defined as crude enzyme solution.

Subsequently, ammonium sulfate was added to the crude enzyme solution to 60-% saturation for salting out. The resulting precipitate was recovered by centrifugation, and then dissolved again in 50 mM potassium phosphate buffer, pH 7.5. Furthermore, the resulting solution was subjected to desalting process by gel filtration by Sephadex G-25 (Amersham Biosciences). Thereafter, the resulting solution was applied to HiTrap Q HP column (Amersham Biosciences), rinsed with 0.2 M NaCl, and eluted on a linear 0.2 M-0.6 M NaCl gradient.

Further, fractions with the glycerol kinase activity were collected, to which ammonium sulfate was added to 20% saturation. Insoluble matters were removed by centrifugation. The enzyme solution was applied to HiTrap Phenyl FF column (Amersham Biosciences) buffered with 50 mM potassium phosphate buffer of pH 7.5 containing ammonium sulfate at 20% saturation, rinsed with the same buffer and eluted by a linear gradient of ammonium sulfate from 20% saturation to 0% saturation. The fraction of the glycerol kinase activity was recovered and desalted by Sephadex G-25 gel filtration, to recover a purified enzyme sample. The purification results are shown in FIG. 9.

The protein purified by the method indicated an almost uniform band with a relative activity of about 41.2 U/mg-protein. The concentration of the protein was calculated approximately in the same manner as in Reference Example 1. The molecular weight of the subunit estimated by SDS-PAGE was about 55,000, while the molecular weight of the intact enzyme after gel filtration with TSK-G3000 SW (7.6-mm diameter and 30-cm height manufactured by Tosoh Corporation) was about 176,000.

Figure 2:
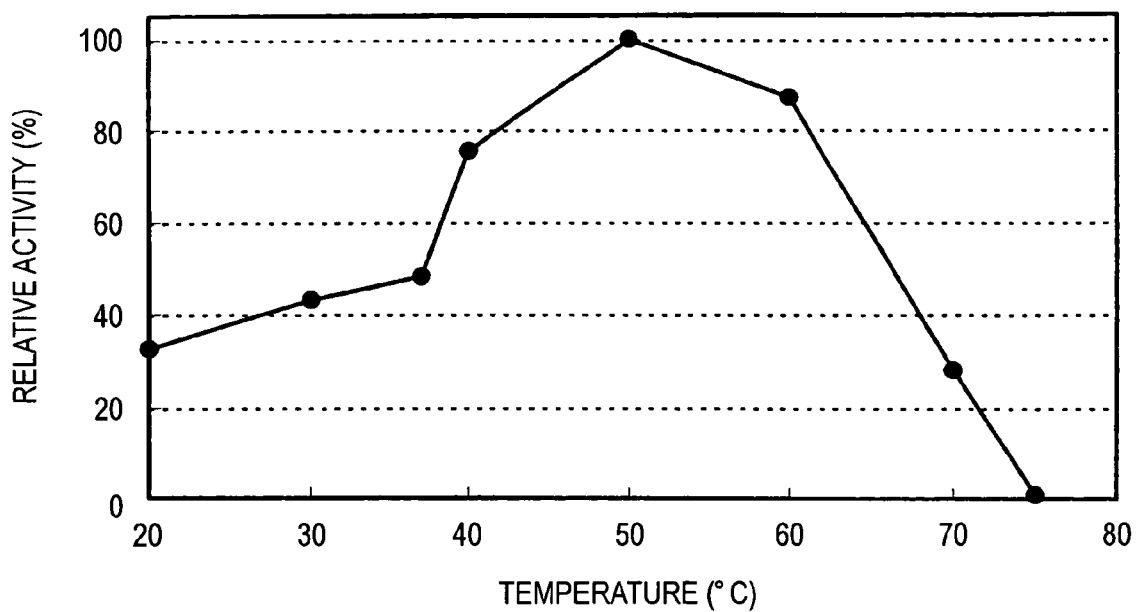
FIG. 2 shows the relation between the reaction temperature of glycerol kinase obtained in Example of the present invention and the relative activity thereof (namely, optimum temperature). Glycerol kinase activity was assayed after reaction in 50 mM HEPES buffer, pH 7.9 at each temperature for 5 minutes. The horizontal axis shows temperature, while the vertical axis shows relative activity.
Figure 3:
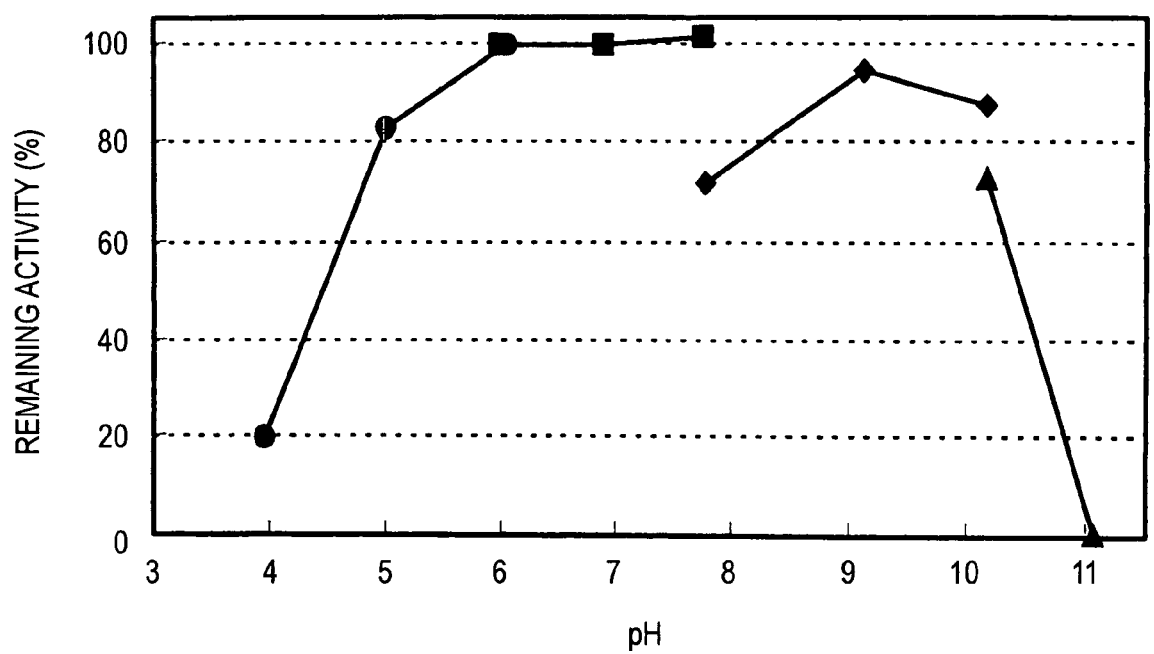
FIG. 3 shows the pH stability of glycerol kinase obtained in Example of the present invention. Glycerol kinase was dissolved in each of 50 mM buffers to become about 10 U/ml and stored at 25° C. for 20 hours. Subsequently, glycerol kinase activity was assayed to determine remaining activity. The horizontal axis shows pH, while the vertical axis shows remaining activity. Black circles express the reaction in the presence of acetate buffer; black squares express the reaction in the presence of potassium phosphate buffer; black diamonds express the reaction in the presence of CHES buffer; black triangles express the reaction in the presence of CAPS buffer.
Figure 4:
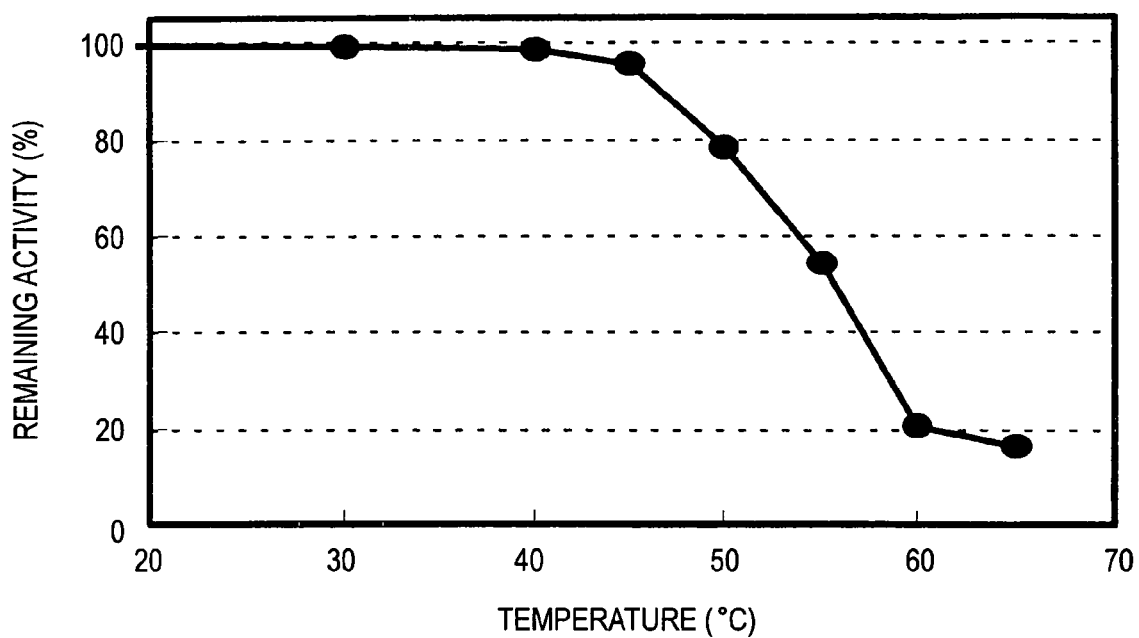
FIG. 4 shows the thermal stability of glycerol kinase obtained in an Example of the present invention. Glycerol kinase was dissolved in 50 mM potassium phosphate buffer of pH 7.5 to become about 10 U/ml and stored at each temperature for 15 minutes. Subsequently, glycerol kinase activity was assayed to determine the remaining activity. The horizontal axis shows temperature, while the vertical axis shows remaining activity.

The glycerol kinase obtained by the method had the following characteristic features.
(1) Function: Catalyzing the following reaction. Glycerol+ATP↔Glycerol-3-phosphoric acid+ADP
(2) Working pH: Relation between reaction pH and relative activity is shown in FIG. 1. Optimal pH was about 10.0.
(3) Working temperature: Relation between reaction temperature and relative activity is shown in FIG. 2. Optimal temperature: about 50° C. (reaction in 20 mM HEPES buffer of pH 7.9 for 5 minutes)
(4) pH stability: pH stability is shown in FIG. 3. Stable at about 6.0 to 10.0 (within the range, 90% or more of the activity remains even at 25° C. for 20 hours).
(5) Thermal stability: Thermal stability is shown in FIG. 4. Stable at about 45° C. or less (within the range, 90% or more of the activity remains even after 15-min treatment in 50 mM potassium phosphate buffer of pH 7.5).
(6) Molecular weight: about 55,000 (SDS-PAGE), about 176,000 (gel filtration)
(7) Km value: about $6.9 \times 10^{-6}$ M (glycerol), about $1.11 \times 10^{-4}$ M (ATP)

Figure 5:
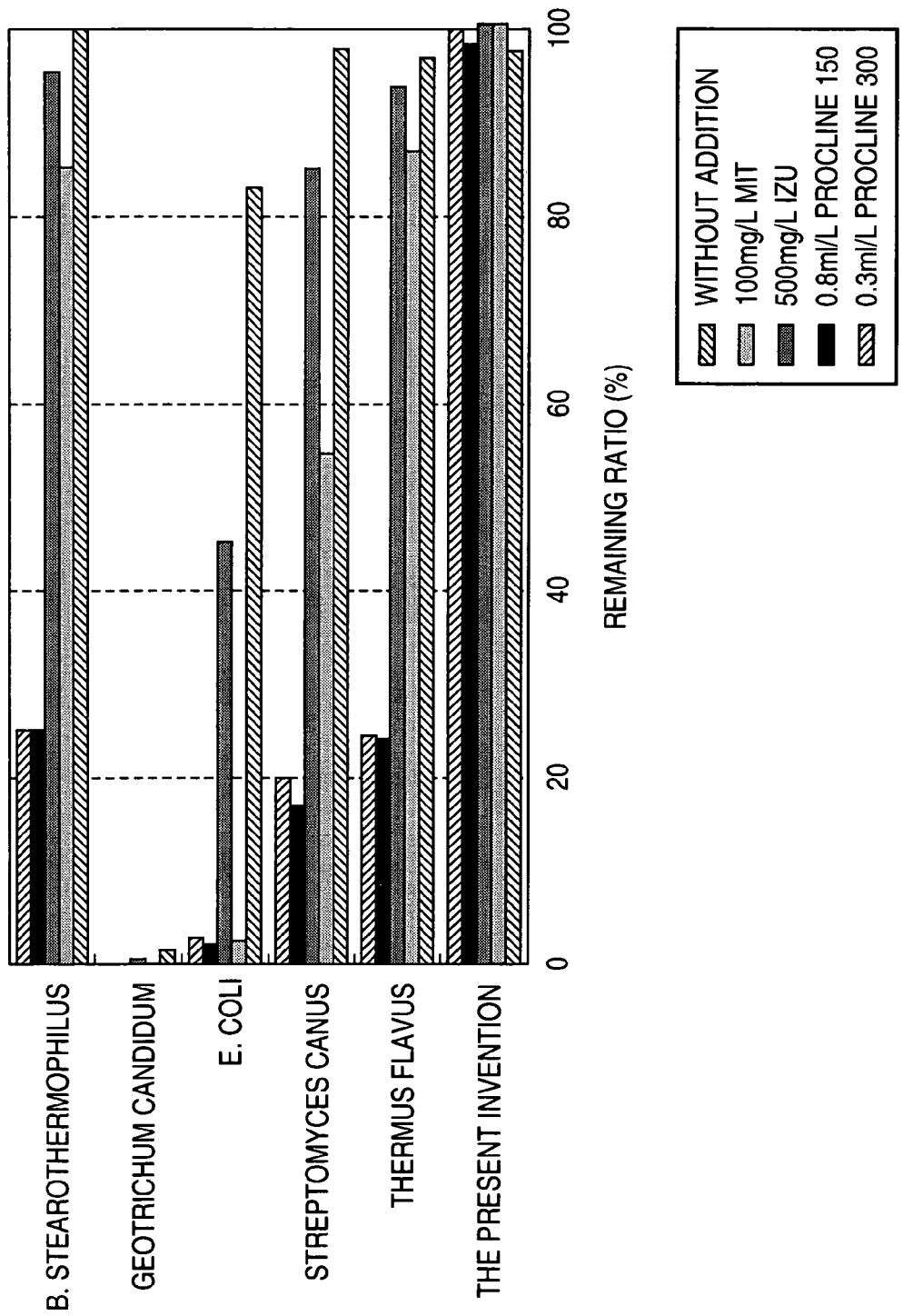
FIG. 5 shows comparative data of remaining activity ratio (namely, resistance against preservative under storage at 4° C.) of the glycerol kinase obtained in an Example of the present invention and a glycerol kinase derived from various other microorganisms when they coexist with various preservatives at 4° C. After dissolving glycerol kinase from each origin in 50 mM potassium phosphate buffer of pH 7.5 to become about 5 U/ml, each preservative was added at a concentration shown in the figure and stored at 4° C. for one week, to assay the remaining activity. The horizontal axis shows remaining activity ratio, while the vertical axis shows the origin of glycerol kinase. The remaining activity ratio of the enzyme from each origin is shown in the order from the top as the activity when 0.3 mM ProClin® 300 is present, 0.8 nM ProClin® 150 is present, 500 mg/L IZU is present, 100 mg/L MIT is present and no preservative is added.
Figure 6:
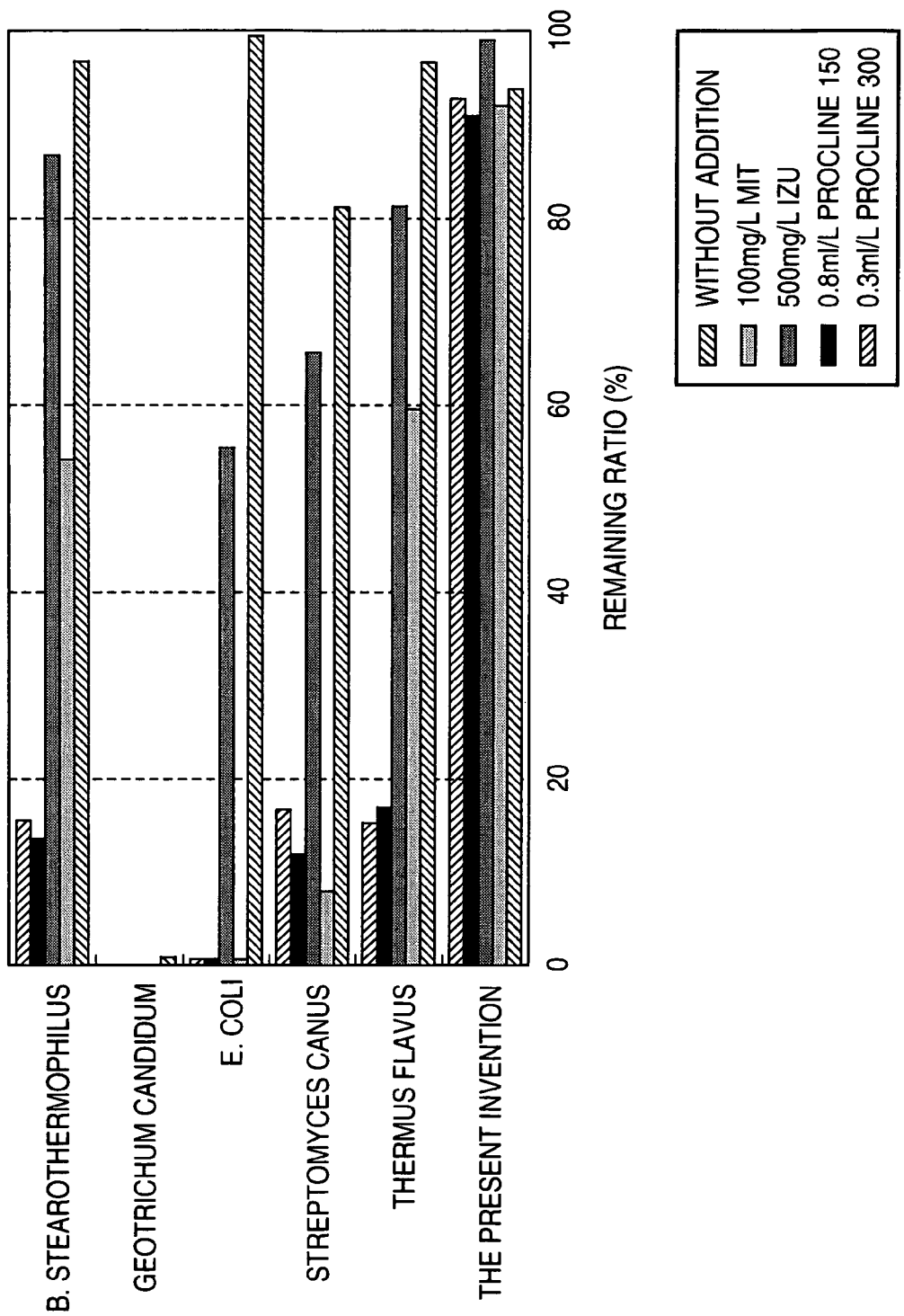
FIG. 6 shows comparative data of remaining activity ratio (namely, resistance against preservative under storage at 25° C.) of the glycerol kinase obtained in an Example of the present invention and a glycerol kinase derived from various other microorganisms when they coexist with various preservatives at 25° C. After dissolving glycerol kinase from each origin in 50 mM potassium phosphate buffer of pH 7.5 to become about 5 U/ml, each preservative was added at a concentration shown in the figure and stored at 25° C. for one week to assay the remaining activity. The horizontal axis shows remaining activity ratio, while the vertical axis shows the origin of glycerol kinase. The remaining activity ratio of the enzyme from each origin is shown in the order from the top as the activity when 0.3 mM ProClin® 300 is present, 0.8 mM ProClin® 150 is present, 500 mg/L IZU is present, 100 mg/L MIT is present and no preservative is added.

The Km values of glycerol and ATP were calculated according to the Lineweaver-Burk equation according to the method described in the section "Method for assaying glycerol kinase activity" <method 1>, wherein the concentration of glycerol or ATP was changed to assay the glycerol kinase activity at each substrate concentration.
(8) Relative activity: About 41.2 U/mg
(9) Resistance against the presence of preservative: Remaining activity ratio in coexistence with 100 mg/L MIT in 50 mM potassium phosphate buffer of pH 7.5 is shown in FIGS. 5 and 6. The activity was assayed according to the method 1.

The remaining activity ratios were almost 100% after storage at 4° C. for one week and about 92% after storage at 25° C. for one week. The remaining activity ratio in coexistence with other preservatives are also shown. Glycerol kinase from other origins as comparative subject was purchased from Sigma Aldrich Japan, except for glycerol kinase from *Thermus flavus* (manufactured by Toyobo Co., Ltd.). Additionally, N-methylisothiazolone (abbreviated as MIT) and imidazolidinylurea (abbreviated as IZU) among the preservatives used were purchased from Roche Diagnostics, while ProClin® 150 and ProClin® 300 were purchased from Sigma Aldrich, Japan.

The glycerol kinase of the present invention kept a remaining activity ratio of 90% or more even after storage at 25° C. for one week.

Figure 7:
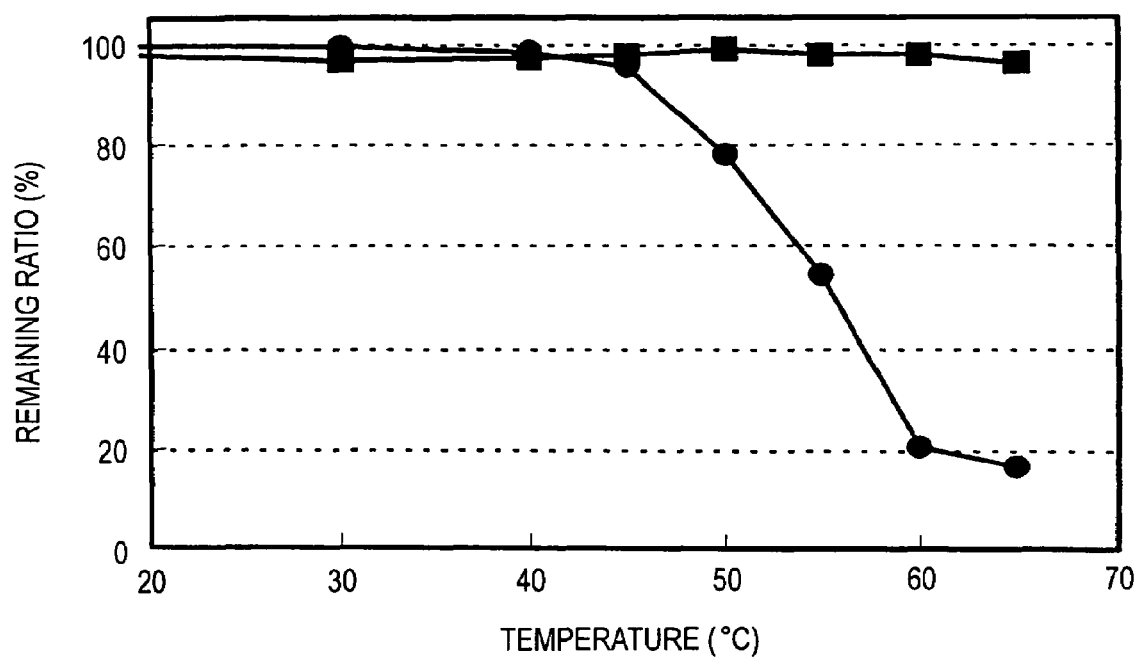
FIG. 7 shows comparative data of the thermal stability of the glycerol kinase obtained in an Example of the present invention and a glycerol kinase derived from *Thermus flavus*. After dissolving the glycerol kinase in 50 mM potassium phosphate buffer of pH 7.5 to become about 10 U/ml, glycerol kinases were stored at each temperature for 15 minutes to assay the remaining activity. The horizontal axis shows temperature, while the vertical axis shows remaining activity ratio. Black circle expresses glycerol kinase of the present invention; black squares expresses glycerol kinase from *Thermus flavus*.

Additionally, FIG. 7 shows comparative thermal stability data with that from *Thermus flavus* as comparative example. Although the glycerol kinase derived from *Thermus flavus* had apparently high thermal stability compared with the glycerol kinase of the present invention, the glycerol kinase of the present invention is shown to have high stability in the coexistence of preservatives. It is thus indicated that the glycerol kinase of the present invention has high resistance against preservatives.

INDUSTRIAL APPLICABILITY

In accordance with the present invention, the gene encoding new glycerol kinase which has high resistance against preservatives compared with known glycerol kinase was isolated, to establish a method for preparing the enzyme by gene recombination technique, which can be applied to glycerol assay.

The invention claimed is:

1. An isolated protein that consist of the amino acid sequence depicted in SEQ ID NO:1.

2. An isolated protein comprising the amino acid sequence depicted in SEQ ID NO:1.

3. A composition comprising:
   an isolated protein comprising the amino acid sequence depicted in SEQ ID NO:1; and
   a preservative.

4. The composition of claim 3, wherein the preservative is selected from the group consisting of ProClin® 150, ProClin® 300, imidazolidinylurea (IZU), and N-methylisothiazolone (MIT).

* * * * *

SEQUENCE LISTING

<160> NUMBER OF SEQ ID NOS: 6

<210> SEQ ID NO 1
<211> LENGTH: 505
<212> TYPE: PRT
<213> ORGANISM: Cellulomonas sp. JCM2471

<400> SEQUENCE: 1

Met Ala Asp Tyr Val Leu Ala Ile Asp Gln Gly Thr Thr Ser Ser Arg
1               5                   10                  15

Ala Ile Val Phe Asn His Ser Gly Glu Ile Tyr Ser Thr Gly Gln Leu
            20                  25                  30

Glu His Asp Gln Ile Phe Pro Arg Ala Gly Trp Val Glu His Asn Pro
        35                  40                  45

Glu Gln Ile Trp Asn Asn Val Arg Glu Val Val Gly Leu Ala Leu Thr
    50                  55                  60

Arg Gly Asn Leu Thr His Glu Asp Ile Ala Ala Val Gly Ile Thr Asn

```
                65                  70                  75                  80
Gln Arg Glu Thr Ala Val Val Trp Asp Lys Thr Thr Gly Lys Pro Val
                        85                  90                  95
Tyr Asn Ala Ile Val Trp Gln Asp Thr Arg Thr Gln Lys Ile Val Asp
                100                 105                 110
Glu Leu Gly Gly Asp Glu Gly Ala Glu Lys Tyr Lys Ser Ile Val Gly
                115                 120                 125
Leu Pro Leu Ala Thr Tyr Phe Ser Gly Pro Lys Ile Lys Trp Ile Leu
                130                 135                 140
Asn Asn Val Glu Gly Ala Arg Glu Lys Ala Glu Lys Gly Asp Leu Leu
145                 150                 155                 160
Phe Gly Asn Thr Asp Thr Trp Val Leu Trp Asn Met Thr Gly Gly Thr
                165                 170                 175
Glu Gly Gly Val His Val Thr Asp Val Thr Asn Ala Ser Arg Thr Met
                180                 185                 190
Leu Met Asp Leu Asp Thr Leu Ser Trp Arg Glu Asp Ile Ala Ala Asp
                195                 200                 205
Met Gly Ile Pro Leu Ser Met Leu Pro Asp Ile Arg Ser Ser Ser Glu
210                 215                 220
Val Tyr Gly His Gly Arg Pro Arg Gly Leu Val Pro Gly Val Pro Ile
225                 230                 235                 240
Ala Gly Ile Leu Gly Asp Gln Gln Ala Ala Thr Phe Gly Gln Ala Cys
                245                 250                 255
Phe Glu Val Gly Gln Ala Lys Asn Thr Tyr Gly Thr Gly Asn Phe Leu
                260                 265                 270
Leu Leu Asn Thr Gly Thr Glu Lys Val Met Ser Lys Asn Gly Leu Leu
                275                 280                 285
Thr Thr Val Cys Tyr Lys Ile Gly Asp Ala Pro Ala Val Tyr Ala Leu
                290                 295                 300
Glu Gly Ser Ile Ala Val Thr Gly Ser Leu Val Gln Trp Leu Arg Asp
305                 310                 315                 320
Asn Leu Gly Met Phe Glu Asp Ala Pro Asp Val Glu Trp Leu Ala Gly
                325                 330                 335
Lys Val Gln Asp Asn Gly Gly Ala Tyr Phe Val Pro Ala Phe Ser Gly
                340                 345                 350
Leu Phe Ala Pro Tyr Trp Arg Pro Asp Ala Arg Gly Ala Leu Val Gly
                355                 360                 365
Leu Thr Arg Tyr Val Asn Arg Asn His Ile Ala Arg Ala Ala Leu Glu
                370                 375                 380
Ala Thr Ala Phe Gln Ser Arg Glu Val Val Asp Ala Met Asn Ala Asp
385                 390                 395                 400
Ser Gly Val Asp Leu Thr Glu Leu Arg Val Asp Gly Gly Met Val Ala
                405                 410                 415
Asn Glu Leu Leu Met Gln Phe Gln Ala Asp Gln Leu Gly Val Asp Val
                420                 425                 430
Val Arg Pro Lys Val Ala Glu Thr Thr Ala Leu Gly Ala Ala Tyr Ala
                435                 440                 445
Ala Gly Ile Ala Val Gly Phe Trp Lys Gly Glu Gln Asp Val Ile Asp
                450                 455                 460
Asn Trp Ala Glu Asp Lys Arg Trp Ser Pro Ser Met Glu Ser Gly Glu
465                 470                 475                 480
Arg Glu Arg Leu Tyr Arg Asn Trp Lys Lys Ala Val Thr Lys Thr Met
                485                 490                 495
```

Glu Trp Val Asp Glu Asp Val Glu Gln
            500                 505

<210> SEQ ID NO 2
<211> LENGTH: 1515
<212> TYPE: DNA
<213> ORGANISM: Cellulomonas sp. JCM2471
<220> FEATURE:
<221> NAME/KEY: CDS
<222> LOCATION: (1)...(1515)

<400> SEQUENCE: 2

| | |
|---|---|
| atg gcc gac tac gtt ctc gcc atc gac cag ggg acc acg agc tcc cgg<br>Met Ala Asp Tyr Val Leu Ala Ile Asp Gln Gly Thr Thr Ser Ser Arg<br>1               5                   10                  15 | 48 |
| gcc atc gtc ttc aac cac tcc ggg gag atc tac tcc acc ggg cag ctc<br>Ala Ile Val Phe Asn His Ser Gly Glu Ile Tyr Ser Thr Gly Gln Leu<br>            20                  25                  30 | 96 |
| gag cac gac cag atc ttc ccg cgc gcg ggc tgg gtc gag cac aac ccc<br>Glu His Asp Gln Ile Phe Pro Arg Ala Gly Trp Val Glu His Asn Pro<br>        35                  40                  45 | 144 |
| gag cag atc tgg aac aac gtg cgc gag gtc gtc ggt ctc gcc ctc acc<br>Glu Gln Ile Trp Asn Asn Val Arg Glu Val Val Gly Leu Ala Leu Thr<br>    50                  55                  60 | 192 |
| cga ggc aac ctc acg cac gag gac atc gcg gcc gtc ggc atc acg aac<br>Arg Gly Asn Leu Thr His Glu Asp Ile Ala Ala Val Gly Ile Thr Asn<br>65                  70                  75                  80 | 240 |
| cag cgc gag acg gcc gtc gtc tgg gac aag acc acg ggc aag ccc gtc<br>Gln Arg Glu Thr Ala Val Val Trp Asp Lys Thr Thr Gly Lys Pro Val<br>                85                  90                  95 | 288 |
| tac aac gcc atc gtc tgg cag gac acg cgc acc cag aag atc gtc gac<br>Tyr Asn Ala Ile Val Trp Gln Asp Thr Arg Thr Gln Lys Ile Val Asp<br>            100                 105                 110 | 336 |
| gag ctc ggc ggc gac gag ggc gcc gag aag tac aag tcg atc gtc ggc<br>Glu Leu Gly Gly Asp Glu Gly Ala Glu Lys Tyr Lys Ser Ile Val Gly<br>        115                 120                 125 | 384 |
| ctg ccg ctc gcc acc tac ttc tcc ggc ccg aag atc aag tgg atc ctc<br>Leu Pro Leu Ala Thr Tyr Phe Ser Gly Pro Lys Ile Lys Trp Ile Leu<br>    130                 135                 140 | 432 |
| gac aac gtc gag ggt gcg cgc gag aag gcc gag aag ggc gac ctg ctg<br>Asp Asn Val Glu Gly Ala Arg Glu Lys Ala Glu Lys Gly Asp Leu Leu<br>145                 150                 155                 160 | 480 |
| ttc ggc aac acc gac acg tgg gtg ctg tgg aac atg acg ggc ggc acc<br>Phe Gly Asn Thr Asp Thr Trp Val Leu Trp Asn Met Thr Gly Gly Thr<br>                165                 170                 175 | 528 |
| gag ggc ggc gtg cac gtc acc gac gtg acc aac gcg tcg cgc acg atg<br>Glu Gly Gly Val His Val Thr Asp Val Thr Asn Ala Ser Arg Thr Met<br>            180                 185                 190 | 576 |
| ctc atg gac ctc gac acg ctc tcc tgg cgc gag gac atc gcc gcc gac<br>Leu Met Asp Leu Asp Thr Leu Ser Trp Arg Glu Asp Ile Ala Ala Asp<br>        195                 200                 205 | 624 |
| atg ggc atc ccg ctg tcg atg ctc ccc gac atc cgg tcg tcg tcc gag<br>Met Gly Ile Pro Leu Ser Met Leu Pro Asp Ile Arg Ser Ser Ser Glu<br>    210                 215                 220 | 672 |
| gtc tac ggc cac ggg cgc ccg cgc ggc ctc gtc ccc ggc gtc ccg atc<br>Val Tyr Gly His Gly Arg Pro Arg Gly Leu Val Pro Gly Val Pro Ile<br>225                 230                 235                 240 | 720 |
| gcc ggc atc ctc ggc gac cag cag gca gcc acg ttc ggc cag gcg tgc<br>Ala Gly Ile Leu Gly Asp Gln Gln Ala Ala Thr Phe Gly Gln Ala Cys<br>                245                 250                 255 | 768 |

```
ttc gag gtc ggc cag gcc aag aac acc tac ggc acc ggc aac ttc ctg       816
Phe Glu Val Gly Gln Ala Lys Asn Thr Tyr Gly Thr Gly Asn Phe Leu
        260                 265                 270 ctg ctc aac acg ggc acg gag aag gtc atg agc aag aac ggc ctg ctc       864
Leu Leu Asn Thr Gly Thr Glu Lys Val Met Ser Lys Asn Gly Leu Leu
    275                 280                 285 acg acg gtc tgc tac aag atc ggc gac gcg ccc gcg gtg tac gcg ctc       912
Thr Thr Val Cys Tyr Lys Ile Gly Asp Ala Pro Ala Val Tyr Ala Leu
290                 295                 300 gag ggc tcg atc gcc gtg acc ggc tcg ctc gtg cag tgg ctc cgc gac       960
Glu Gly Ser Ile Ala Val Thr Gly Ser Leu Val Gln Trp Leu Arg Asp
305                 310                 315                 320 aac ctg ggc atg ttc gag gac gcg ccc gac gtc gag tgg ctc gcg ggc      1008
Asn Leu Gly Met Phe Glu Asp Ala Pro Asp Val Glu Trp Leu Ala Gly
            325                 330                 335 aag gtc cag gac aac ggc ggc gcc tac ttc gtg ccg gcg ttc tcc ggc      1056
Lys Val Gln Asp Asn Gly Gly Ala Tyr Phe Val Pro Ala Phe Ser Gly
        340                 345                 350 ctg ttc gcg ccc tac tgg cgg ccc gac gcg cgc ggc gcg ctc gtc ggc      1104
Leu Phe Ala Pro Tyr Trp Arg Pro Asp Ala Arg Gly Ala Leu Val Gly
    355                 360                 365 ctc acg cgg tac gtc aac cgc aac cac atc gcg cgc gcc gcg ctc gag      1152
Leu Thr Arg Tyr Val Asn Arg Asn His Ile Ala Arg Ala Ala Leu Glu
370                 375                 380 gcg acg gcg ttc cag agc cgc gag gtc gtc gac gcg atg aac gcc gac      1200
Ala Thr Ala Phe Gln Ser Arg Glu Val Val Asp Ala Met Asn Ala Asp
385                 390                 395                 400 tcg ggc gtc gac ctc acc gag ctg cgc gtc gac ggc ggc atg gtc gcc      1248
Ser Gly Val Asp Leu Thr Glu Leu Arg Val Asp Gly Gly Met Val Ala
            405                 410                 415 aac gag ctc ctc atg cag ttc cag gcc gac cag ctc ggc gtc gac gtc      1296
Asn Glu Leu Leu Met Gln Phe Gln Ala Asp Gln Leu Gly Val Asp Val
        420                 425                 430 gtg cgg ccc aag gtc gcc gag acg acg gcg ctc ggt gcc gcg tac gcc      1344
Val Arg Pro Lys Val Ala Glu Thr Thr Ala Leu Gly Ala Ala Tyr Ala
    435                 440                 445 gcg ggc atc gcc gtc ggc ttc tgg aag ggc gag cag gac gtc atc gac      1392
Ala Gly Ile Ala Val Gly Phe Trp Lys Gly Glu Gln Asp Val Ile Asp
450                 455                 460 aac tgg gcc gag gac aag cgc tgg agc ccg tcg atg gag tcc ggc gag      1440
Asn Trp Ala Glu Asp Lys Arg Trp Ser Pro Ser Met Glu Ser Gly Glu
465                 470                 475                 480 cgc gag cgg ctg tac cgc aac tgg aag aag gcc gtg acg aag acg atg      1488
Arg Glu Arg Leu Tyr Arg Asn Trp Lys Lys Ala Val Thr Lys Thr Met
            485                 490                 495 gag tgg gtc gac gag gac gtg gag cag                                   1515
Glu Trp Val Asp Glu Asp Val Glu Gln
        500                 505

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3
tacgtsctsg csatcgacca ggg                                                23

<210> SEQ ID NO 4
<211> LENGTH: 27
```

-continued

```
<212> TYPE: DNA
<213> ORGANISM: Artificial Sequence
<220> FEATURE:
<223> OTHER INFORMATION: primer

<400> SEQUENCE: 4
ttcttgtgsa tgccstgscc sacgaag                                           27

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
atatcgttgc gctcgaccag ggc                                               23

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
tcgtgttctt cccacgccat cgc                                               23
```